(12) United States Patent
Weston et al.

(10) Patent No.: US 10,675,389 B2
(45) Date of Patent: Jun. 9, 2020

(54) INSTRUCTIONAL MEDICAL TREATMENT SYSTEM

(71) Applicant: Smith & Nephew, Inc., Memphis, TN (US)

(72) Inventors: Richard Scott Weston, Carlsbad, CA (US); Farhad Bybordi, Boynton Beach, FL (US)

(73) Assignee: Smith & Nephew, Inc., Memphis, TN (US)

(*) Notice: Subject to any disclaimer, the term of this patent is extended or adjusted under 35 U.S.C. 154(b) by 155 days.

(21) Appl. No.: 15/693,267

(22) Filed: Aug. 31, 2017

(65) Prior Publication Data

US 2017/0360999 A1 Dec. 21, 2017
US 2018/0177927 A2 Jun. 28, 2018

Related U.S. Application Data

(63) Continuation of application No. 14/886,987, filed on Oct. 19, 2015, now Pat. No. 9,775,935, which is a
(Continued)

(51) Int. Cl.
*A61M 1/00* (2006.01)
*A61M 27/00* (2006.01)

(52) U.S. Cl.
CPC ........ *A61M 1/0031* (2013.01); *A61M 1/0023* (2013.01); *A61M 1/0088* (2013.01);
(Continued)

(58) Field of Classification Search
CPC .. A61M 1/0088; A61M 27/00; A61M 1/0031; A61M 1/0023
(Continued)

(56) References Cited

U.S. PATENT DOCUMENTS 4,382,441 A 5/1983 Svedman
4,710,165 A 12/1987 McNeil et al.
(Continued)

FOREIGN PATENT DOCUMENTS

| GB | 2195255 A | 4/1988 |
|----|-----------|--------|
| WO | WO 1996/05873 | 2/1996 |
| WO | WO 2008/036345 | 3/2008 |

OTHER PUBLICATIONS

U.S. Appl. No. 60/845,993, filed Sep. 16, 2006, Locke et al.
(Continued)

*Primary Examiner* — Phillip A Gray
(74) *Attorney, Agent, or Firm* — Knobbe, Martens, Olson & Bear LLP

(57) ABSTRACT

The present invention discloses an appliance for administering medical treatment to a person, as well as methods of using the appliance. In various embodiments, the appliance may be comprised of a medical device, an electronic processor, an electronic display (such as a liquid crystal display (LCD)), an audio output device (such as a piezoelectric speaker/microphone), electronic controls for controlling the operation of the electronic processor, and an electronic input receptacle (such as a DVD drive or USB port) adapted to receive and electronically access an electronic storage device (such as a DVD or flash memory device). The electronic processor or electronic storage device or both have information related to use and operation of the medical device digitally stored therein, so that the user of the appliance has ready access to instructional materials. Thus, the appliance includes an internal system for instructing the user in the use of the medical device.

28 Claims, 2 Drawing Sheets

Related U.S. Application Data continuation of application No. 14/505,804, filed on Oct. 3, 2014, now Pat. No. 9,186,446, which is a continuation of application No. 11/784,021, filed on Apr. 5, 2007, now Pat. No. 8,852,149.

(60) Provisional application No. 60/789,817, filed on Apr. 6, 2006.

(52) U.S. Cl.
CPC ......... *A61M 27/00* (2013.01); *A61M 2205/18* (2013.01); *A61M 2205/3331* (2013.01); *A61M 2205/502* (2013.01); *A61M 2205/505* (2013.01); *A61M 2205/6018* (2013.01)

(58) Field of Classification Search
USPC ........................................ 604/313, 543, 131
See application file for complete search history.

(56) References Cited

U.S. PATENT DOCUMENTS

| | | | |
|---|---|---|---|
| 4,902,277 | A | 2/1990 | Marhies et al. |
| 4,969,880 | A | 11/1990 | Zamierowski |
| 5,115,472 | A | 5/1992 | Park et al. |
| 5,636,643 | A | 6/1997 | Argenta |
| 5,645,081 | A | 7/1997 | Argenta |
| 6,142,982 | A | 11/2000 | Hunt |
| 6,398,767 | B1 | 6/2002 | Fleischmann |
| 6,458,109 | B1 | 10/2002 | Henley et al. |
| 6,566,833 | B2 | 5/2003 | Bartlett |
| 6,764,462 | B2 | 7/2004 | Risk, Jr. et al. |
| 7,004,915 | B2 | 2/2006 | Boynton et al. |
| 7,022,113 | B2 * | 4/2006 | Lockwood .......... A61M 1/0031 601/6 |
| 7,108,683 | B2 | 9/2006 | Zamierowski |
| 7,128,735 | B2 | 10/2006 | Weston |
| 7,216,651 | B2 | 5/2007 | Argenta et al. |
| 7,322,971 | B2 | 1/2008 | Shehada |
| 7,494,482 | B2 | 2/2009 | Orgill et al. |
| 7,763,000 | B2 | 7/2010 | Risk, Jr. et al. |
| 8,852,149 | B2 | 10/2014 | Weston et al. |
| 8,870,812 | B2 | 10/2014 | Alberti et al. |
| 9,186,446 | B2 | 11/2015 | Weston et al. |
| 9,545,466 | B2 | 1/2017 | Locke et al. |
| 2001/0049609 | A1 | 12/2001 | Girouard et al. |
| 2002/0161346 | A1 | 10/2002 | Lockwood et al. |
| 2002/0183616 | A1 | 12/2002 | Toews et al. |
| 2003/0071893 | A1 * | 4/2003 | Miller .................. A61B 3/0058 348/42 |
| 2003/0097100 | A1 | 5/2003 | Watson |
| 2007/0014837 | A1 | 1/2007 | Johnson et al. |
| 2007/0276195 | A1 | 11/2007 | Xu et al. |
| 2007/0276309 | A1 | 11/2007 | Xu et al. |
| 2008/0071216 | A1 | 3/2008 | Locke et al. |
| 2016/0095965 | A1 | 4/2016 | Weston et al. |

OTHER PUBLICATIONS

Bagautdinov, "Variant of External Vacuum Aspiration in the Treatment of Purulent Diseases of Soft Tissues," Current Problems in Modern Clinical Surgery, 1986, 4 pages.

Hunteligh Healthcare Limited, WoundAssist TNP Brochure (2007).

Info V.A.C. User Manual—KCI—Dec. 2006, in 76 pages.

Jeter, K. F. et al., "Managing Draining Wounds and Fistulae: New and Established Methods", Chronic Wound Care, Chapter 27, pp. 240-246, 1990.

Zivadinovic, G. et al., "Vacuum Therapy in the Treatment of Peripheral Blood Vessels", Timocki Medicinski Glasnik (Conference Papers of the 5th Timok Medical Days, Majdanpek, 1986), Year XI, Zajecar, 1986, No. 3-4, pp. 161-164.

\* cited by examiner

INSTRUCTIONAL MEDICAL TREATMENT SYSTEM

CROSS REFERENCE TO RELATED APPLICATIONS

This application is a continuation of U.S. patent application Ser. No. 14/886,987, filed on Oct. 19, 2015, which is a continuation of U.S. patent application Ser. No. 14/505,804, filed on Oct. 3, 2014 and issued as U.S. Pat. No. 9,186,446, which claims the benefit of U.S. patent application Ser. No. 11/784,021, filed on Apr. 5, 2007 and issued as U.S. Pat. No. 8,852,149, which claims the benefit of U.S. Provisional Patent Application No. 60/789,817, filed on Apr. 6, 2006. The disclosures of these prior applications are incorporated by reference in their entirety.

BACKGROUND

The present invention generally relates to an appliance and methods that may be used to provide instruction in how to use a medical device to provide medical treatment to a person. More specifically, the present invention is comprised of an appliance that integrates the medical device with other hardware and software that may be used to provide a medical practitioner using the medical device with information regarding the use and operation of the medical device.

As medical technology continues to advance, new medical devices are continually becoming available for use by healthcare practitioners. Because of the relatively large number of these new devices, healthcare practitioners may have difficulty in retaining knowledge regarding the use of the devices. If a healthcare practitioner is unfamiliar with a medical device, patient safety may be compromised if the practitioner is unable to complete, or incorrectly completes, a course of treatment because he or she fails to have adequate knowledge of use of the device.

Keeping apprised of the proper use of new medical devices, however, represents a number of challenges. For example, it is typically difficult for busy healthcare practitioners to find time to read an instruction manual for a medical device. This means of instruction is also inefficient for many people who tend to be more visually oriented. Where a hands-on approach to learning is more efficient, it is often necessary to attend a class or have personal instruction in how to use the device. This may be difficult because of time constraints or scheduling problems. Even if the healthcare practitioner has received instruction in the use of a medical device, problems may arise if significant time has elapsed since the last use of the device. For example, the practitioner may find himself or herself in a position of suddenly realizing that crucial information has been forgotten in the midst of providing treatment using the device. There may be no convenient way to reacquire this missing information, so that patient safety may be compromised as a result.

There is therefore a need for a system that provides efficient instruction regarding the use and operation of medical devices to perform their intended medical treatment. Preferably, this system provides a hands-on approach to learning without the need for a separate training class or personal instruction. The system should also provide ready access to instruction while using the medical device, so that instruction may be readily obtained while the device is in use. Finally, the system should allow the practitioner quick and easy access to the portion of the instructional materials that are necessary.

SUMMARY

The present invention is directed to an appliance and methods that satisfy the needs described above. As described in greater detail below, they have many advantages over existing instructional apparatus and methods when used for their intended purpose, as well as novel features that result in a new instructional appliance and methods that are not anticipated, rendered obvious, suggested, or even implied by any of the prior art apparatus or methods, either alone or in any combination thereof.

In accordance with the present invention, an appliance is provided for administering medical treatment to a person, in which the appliance also provides ready and convenient access to instruction in the use of the appliance in a manner that overcomes the disadvantages of currently existing apparatus. In one embodiment of the present invention, the appliance is comprised of a medical device, a electronic processor, and display means, which are described in more detail below. The medical device is generally adapted to provide the desired medical treatment to the person. The electronic processor is positioned on or within the medical device, and is adapted so that video content relating to use and operation of the medical device is digitally stored within the electronic processor. The display means, which are described in more detail below, visually display the video content digitally stored within the electronic processor. The display means are also positioned on a surface of the medical device, and are electronically connected to the electronic processor. The display means are capable of displaying the video content so that the user of the appliance has access to video information regarding use and operation of the medical device.

As a result, the appliance of the present invention meets the needs described above in the Background section. For example, the appliance provides efficient instruction regarding the use and operation of the medical device in performing its intended medical treatment. The video content digitally stored in the electronic processor contains this information. The video content is also typically indexed so that different portions of the stored instructional information may be accessed as desired by the healthcare practitioner. Because the appliance generally provides video instruction, it overcomes the monotony and frustration associated with merely reading an instruction manual. The appliance also provides a hands-on approach to learning without the need for a separate training class or personal instruction. Because the medical device is integrated as a part of the appliance, the appliance provides ready access to instruction while using the medical device. Thus, the practitioner may readily obtain instruction even while using the medical device to provide medical treatment. This may enhance patient safety where instructional information becomes necessary during the course of the treatment. It is to be noted that almost any medical device may be used as a part of the appliance, as long as its physical dimensions and complexity allow for and warrant use of the instructional system encompassed within the appliance.

In some embodiments of the present invention, the display means are comprised of a liquid crystal display. In other embodiments, the appliance is further comprised of electronic control means for electronically controlling the operation of the electronic processor, and the liquid crystal display is comprised of a touch-screen liquid crystal display that is adapted to comprise the electronic control means. The appliance may also further comprise audio output means for audibly broadcasting audio content relating to use and operation of the medical device. The audio output means are positioned on or within the medical device and are electronically connected to the electronic processor. The audio content may be digitally stored within the electronic processor. In some embodiments, the audio output means are comprised of a piezoelectric device. In other embodiments, the medical device is comprised of a vacuum pump that produces suction for use in medical treatment of the person.

The appliance may also be further comprised of electronic input means adapted to receive and electronically access at least one electronic storage device. The electronic input means are positioned on or within the medical device and are electronically connected to the electronic processor. Video content relating to use and operation of the medical device may be digitally stored within the at least one electronic storage device, and the display means is adapted to display this video content. Where the appliance further comprises audio output means, audio content may also be digitally stored within the at least one electronic storage device. In various embodiments, the electronic input means may be comprised of a DVD drive, in which case the at least one electronic storage device is comprised of a DVD. In some embodiments, the appliance further comprises the at least one electronic storage device. In yet other embodiments, the electronic processor is adapted to receive information from the medical device related to the operation of the medical device. This information is in a digital form that can be processed by the electronic processor, and the display means is adapted to display the information.

In other embodiments, the appliance comprises a medical device, an electronic processor positioned on or within the medical device, an electronic display positioned on a surface of the medical device, electronic control means for controlling the operation of the electronic processor (which are described in more detail below), and at least one electronic input receptacle positioned on or within the medical device. The electronic processor is electronically connected to the electronic display, the electronic control means, and the at least one electronic input receptacle. The at least one electronic input receptacle is adapted to receive and electronically access at least one electronic storage device, which has video content relating to use and operation of the medical device digitally stored within it. The electronic display may be comprised of a liquid crystal display. In some embodiments, the electronic display and electronic control means are both comprised of a touch-screen liquid crystal display. The appliance may also further comprise audio output means (which may be a piezoelectric device) adapted to audibly broadcast audio content relating to use and operation of the medical device. The audio content may be digitally stored within the at least one electronic storage device. In these embodiments, the electronic processor may also be adapted to have video content and audio content relating to use and operation of the medical device digitally stored within it. The at least one electronic input receptacle may be comprised of a DVD drive or an USB port and the at least one electronic storage device may be comprised of a DVD and a flash storage device, respectively.

The present invention also includes a method of instructing a user of an appliance how to use and operate the appliance for purposes of providing medical treatment to a person. This method generally comprises the following actions. First, the user gains physical access to the appliance, wherein the appliance is comprised of a medical device, an electronic processor, an electronic display, and electronic control means for controlling the operation of the electronic processor, all of which are described in more detail herein. Next, the user activates the electronic processor by manipulating the electronic control means, so that the video content is displayed on the electronic display. Next, the user visually observes the video content displayed on the electronic display, so that the user has access to information regarding use and operation of the medical device. In some embodiments, the medical device comprises a vacuum pump used to provide suction for purposes of the medical treatment, and the medical treatment comprises negative pressure wound therapy. In other embodiments, the method further comprises the action of the user using the medical device to provide medical treatment to the person.

Another method of the present invention also relates to instructing a user of an appliance in the use and operation of the appliance for purposes of providing medical treatment to a person. This method generally comprises the following actions. First, the user gains physical access to the appliance, wherein the appliance is comprised of a medical device, an electronic processor, an electronic display, electronic control means for controlling the operation of the electronic processor, and electronic input means adapted to receive and electronically access an electronic storage device, all of which are described in more detail herein. Next, the user operably connects the electronic storage device to the electronic input means. The user then activates the electronic processor by manipulating the electronic control means, so that the video content is displayed on the electronic display. Next, the user visually observes the video content displayed on the electronic display, so that the user has access to information regarding use and operation of the medical device. In some embodiments, the medical device comprises a vacuum pump used to provide suction for purposes of the medical treatment, and the medical treatment comprises negative pressure wound therapy. In other embodiments, the method further comprises the action of the user using the medical device to provide medical treatment to the person.

There has thus been outlined, rather broadly, the more primary features of the present invention. There are additional features that are also included in the various embodiments of the invention that are described hereinafter and that form the subject matter of the claims appended hereto. In this respect, it is to be understood that the invention is not limited in its application to the details of construction and to the arrangements of the components set forth in the following description or illustrated in the following drawings. This invention may be embodied in the form illustrated in the accompanying drawings, but the drawings are illustrative only and changes may be made in the specific construction illustrated and described within the scope of the appended claims. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

The foregoing summary, as well as the following detailed description of the preferred embodiments of the present invention, will be better understood when read in conjunction with the appended drawings, in which.

DETAILED DESCRIPTION OF THE PREFERRED EMBODIMENTS

In accordance with the present invention, an appliance and methods for using the appliance are provided for administering medical treatment to a person. The word "person" is to be broadly construed and may encompass animals as well as humans. Although the description of the present invention set forth herein is directed primarily toward use of the appliance and methods for treatment of wounds and other infirmities on a portion of a person's body, the term "medical treatment," as used herein, may also include any other type of treatment or activity conducted for purposes of examination, diagnosis, treatment, cure or relief of any disease, condition or malady, or for other purposes related to the health and well being of the person. Such uses are encompassed within the scope of the present invention to the extent they are included within the scope of the appended claims.

Figure 1:
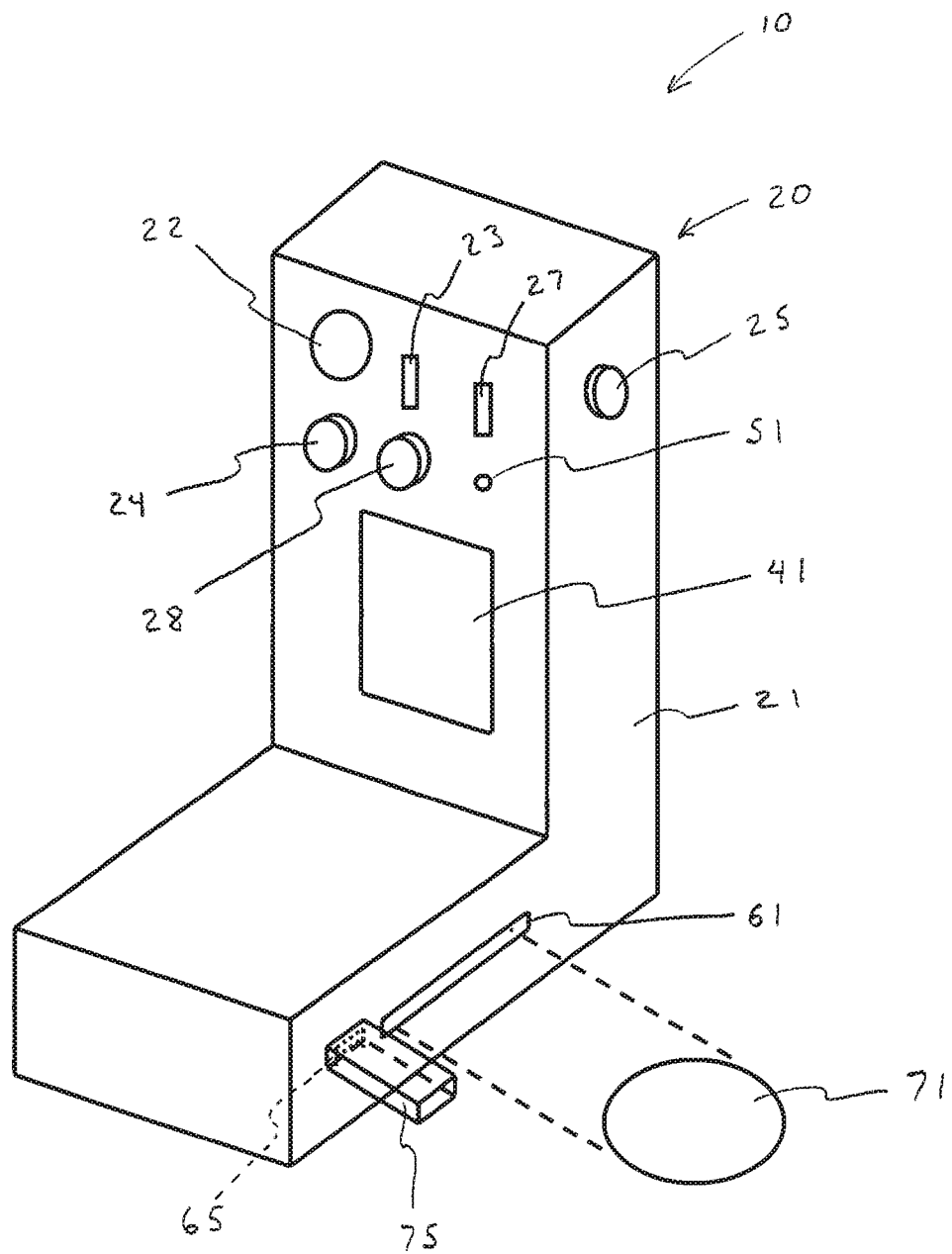
FIG. 1 is a perspective view of an embodiment of an appliance comprising the present invention.

An embodiment of an appliance 10 of the invention is illustrated in perspective view in FIG. 1. A schematic diagram of the appliance 10 of FIG. 1 is set forth in FIG. 2, in which the components of the appliance 10 other than those related to the particular medical device 20 utilized as a part of the appliance 10 are illustrated. It is to be noted that the various components comprising the medical device 20 are dependent upon the type of medical device 20 incorporated as a part of the appliance 10, and are not relevant to the present invention, as described in more detail below. In this embodiment, the appliance 10 is generally comprised of a medical device 20, an electronic processor 30 (illustrated schematically in FIG. 2), display means 40 (illustrated schematically in FIG. 2, and as a liquid crystal display 41 in FIG. 1, which are described in more detail below), audio output means 50 (illustrated schematically in FIG. 2, and as a piezoelectric device 51 in FIG. 1, which are described in more detail below), electronic input means 60 (illustrated schematically in FIG. 2, and as a DVD drive 61 and a Universal Serial Bus (USB) port 65 in FIG. 1, which are described in more detail below), an electronic storage device 70 (illustrated schematically in FIG. 2, and as a DVD 71 and a flash storage device 75 in FIG. 1, which are described in more detail below), and electronic control means 80 (illustrated schematically in FIG. 2, and described in more detail below).

The medical device 20 is adapted to provide medical treatment to a person (not illustrated). In the illustrated embodiment, the medical device 20 is a medical grade vacuum pump 21 that acts as a source of negative pressure for purposes of negative pressure wound therapy. This type of vacuum pump and its use for purposes of negative pressure wound therapy are described in more detail in U.S. Pat. No. 7,128,735, issued to Richard Scott Weston, the disclosure of which is incorporated herein by reference. Generally, the vacuum pump 21 is further comprised of a vacuum gauge 22 to measure negative pressure produced by the vacuum pump 21, an on/off switch 23 for vacuum pump 21 operation, and a knob 24 for control of the negative pressure level to be created by the vacuum pump 21. A connector 25 is used to connect the vacuum pump 21 to one end of a length of flexible tubing (not illustrated and not material for purposes of this disclosure), which is connected at its other end to a wound dressing (not illustrated and not material for purposes of this disclosure). It is to be noted that in other embodiments of the present invention the medical device 20 may be comprised of almost any type of medical device currently known in the relevant art or that may be developed in the relevant art in the future, as long as the medical device 20 has physical dimensions adequate to house the remaining components comprising the appliance 10 and the complexity of use and operation of the medical device 20 is such that instruction in such use and operation may be desirable.

When the user of the appliance 10 desires to receive instruction in the use and operation of the medical device 20, he or she manipulates the electronic control means 80 (as described in more detail below), designating the training materials he or she desires to observe. The video and audio content comprising the training materials are digitally stored within data storage media comprising the electronic processor 30 (as described in more detail below) or on one or more electronic storage devices 70, 71, 75 (as described in more detail below). The electronic processor 30 also controls the operation of the display means 40, 41, the audio output means 50, 51, and the electronic input means 60, 61, 65, all of which are described in more detail below. When electronically directed by the electronic control means 80, the electronic processor 30 calls for and receives the video and audio content that is digitally stored within the data storage media comprising the electronic processor 30 (as described in more detail below) or received from the electronic storage device 70, 71, 75 through the electronic input means 60, 61, 65 (as described in more detail below). The electronic processor 30 then transmits the selected video content to the display means 40, 41, and the selected audio content to the audio output means 50, 51. The user of the appliance 10 is then able to visually observe the video content, as it is displayed on the display means 40, 41, and to hear audio content, as it is broadcast from the audio output means 50, 51.

It is to be noted that the "video content" and "audio content" comprising the training materials, as such terms are used herein, are typically coordinated so that the audio content accompanies the video content, as would be the case in viewing a full-motion video of a person describing how to use a feature of the medical device 20. In some embodiments, however, there may be reasons for including separate video or audio content, such as an audible alarm where the audio output means 50, 51 are also used as a part of the medical device 20, or a visual chart where the display means 40, 41 are also used to display information (such as negative pressure levels over time) related to operation of the medical device 20. Further, the training materials may take any suitable form that may be useful for providing instruction in the use and operation of the medical device 20, such as full-motion video, static photographs, slides, charts, graphs, graphics, drawings, depictions, plans, specifications, or other types of related information or combinations thereof.

Figure 2:
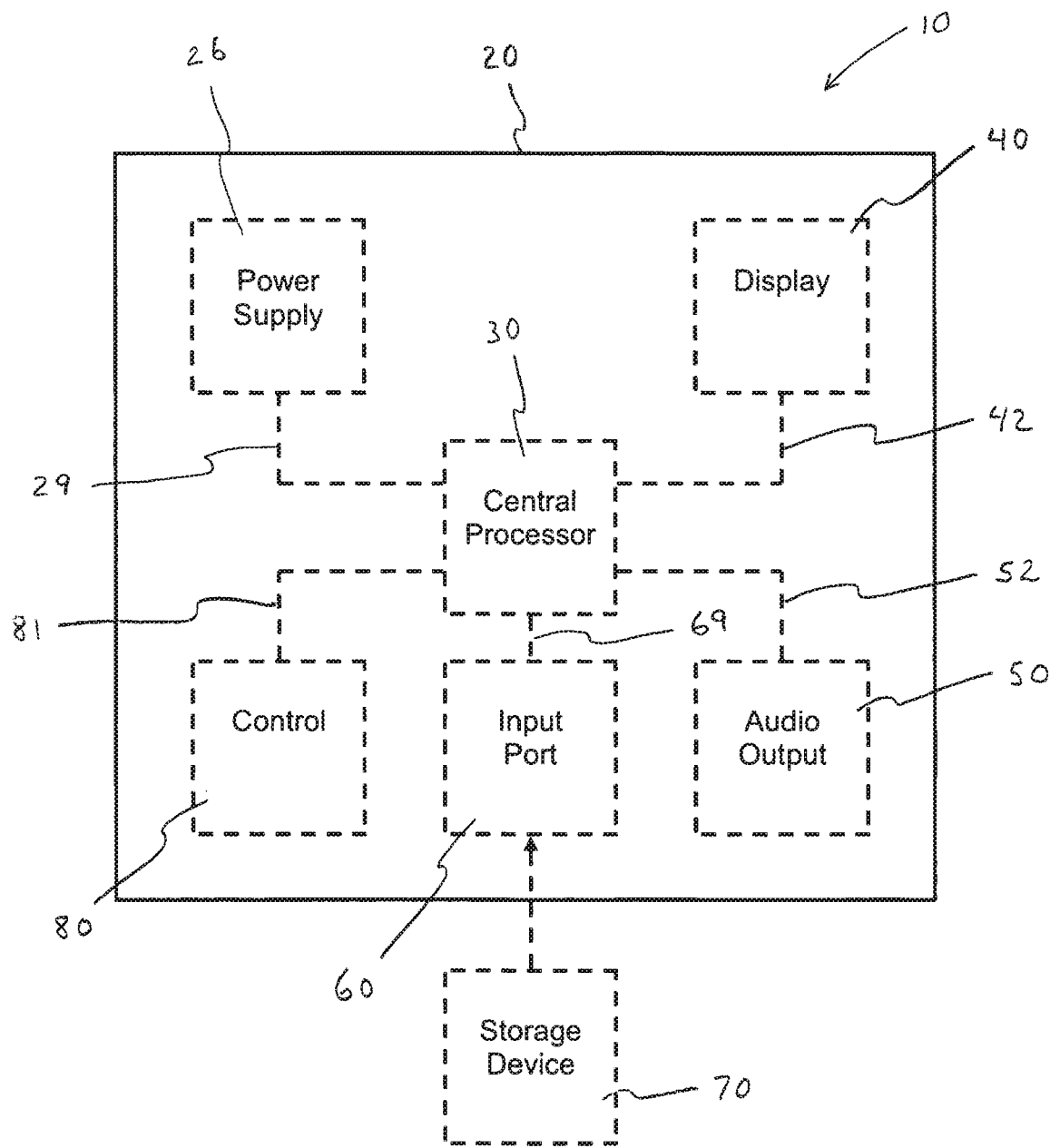
FIG. 2 is a schematic diagram of the embodiment of the appliance illustrated in FIG. 1, in which the components of the appliance other than those related to the particular medical device are illustrated.

The electronic processor 30 of the appliance 10 is illustrated schematically in FIG. 2. The electronic processor 30 is not illustrated in FIG. 1, however, because it is positioned within the casing of the vacuum pump 21. In the embodiment of the invention illustrated in FIG. 1, all of the functions of the electronic processor 30 are performed by a single electronic processor 30. In other embodiments of the invention, however, the various processor-related functions of the electronic processor 30 may be performed by separate electronic processors or combinations of electronic processors. The preferred number of electronic processors comprising the electronic processor 30 depends upon the function or functions to be performed by the electronic processor 30. For example, the electronic processor 30 may be comprised of multiple processors where multiple types of electronic input means 60 are provided. Generally, and referring again to the embodiment of the invention illustrated in FIG. 1 and FIG. 2 as an example, the electronic processor 30 may be comprised of one or more integrated circuits, printed circuits, and hybrid circuits or any combination of such circuits currently known in the relevant art or developed in the relevant art in the future. In addition, passive and active circuit components may be used in conjunction with one or more of such circuits where the functions to be performed by the electronic processor 30 require such components. Such circuits may be constructed of a rigid, semi-rigid, or flexible substrate material.

The type of electronic processor 30 is generally dependent upon the type of display means 40, 41, the type of electronic input means 60, 61, 65, the type of audio output means 50, 51, the type of electronic storage device 70, 71, 75, and the type of electronic control means 80 to be utilized in the appliance 10. For example, the electronic processor 30 includes circuits necessary to electronically operate the display means 40. In the illustrated embodiment of the appliance 10, the electronic processor 30 may include a driver circuit, which is used to develop the voltages appropriate to activate and deactivate the pixels of display means 40 comprised of a liquid crystal display (LCD) 41. The electronic processor 30 may also include a polarity switcher at the output of the driver circuit that selects whether the row or column electrode of the LCD display 41 is to receive the positive polarity, while a row/column selector switch determines which specific row/column pair of the LCD display 41 receives the voltages produced by the polarity switch and the driver circuit. In some embodiments of the invention, the electronic processor 30 may also comprise one or more additional electronic data storage media (not illustrated), which may be comprised of almost any portable data storage media currently known in the relevant art or that may be developed in the relevant art in the future. For example, such data storage media may include one or more additional memory boards or integrated circuits or a part of the integrated circuit or circuits comprising the electronic processor 30. Alternatively, such electronic data storage media may also include one or more of each of the following devices in electronic communication with the circuits comprising the electronic processor 30: optical storage device (such as compact disc, digital versatile disc (sometimes also referred to as digital video disc or "DVD"), hard drive device, flash memory data storage device, or combinations of such devices. The preferred data storage media is dependent upon the types of devices comprising the remaining portions of the appliance 10 (without considering the medical device 20), as well as the type and quantity of audio content and video content to be utilized by the appliance 10. The more preferred data storage media is a hard drive device or flash memory data storage device. The electronic processor 30 may also be adapted to receive information from the medical device 20 in a compatible digital form so that such information may be displayed on the display means 40, 41 or broadcast by the audio output means 50, 51. Such information may include medical device 20 operating parameters (such as periodic pressure level measurements), alarm notifications (such as a low vacuum alarm signal), and other information related to the use, operation and function of the medical device 20.

Preferably, the electronic processor 30 is a modular integrated circuit or combination of integrated circuits, including suitable data storage media, adapted to perform the functions desired of the appliance 10. These functions generally include: (a) electronically interacting with the electronic storage device 70, 71, 75 through the electronic input means 60, 61, 65; (b) receiving, recording, storing, and processing the digital audio content and video content; (c) electronically interacting with the electronic control means 80 to receive electronic instructions from the user; and (d) electronically interacting with the display means 40, 41 to display the video content and with the audio output means 50, 51 to broadcast the audio content. Examples of electronic processors suitable for use as the electronic processor 30 are well known in the relevant art.

The electronic processor 30 may be included as a part of a circuit board (not illustrated) that comprises the medical device 20 (vacuum pump 21). Alternatively, the electronic processor 30 may be positioned in any suitable area within the casing of the vacuum pump 21, may be incorporated as a part of any suitable component (not illustrated) comprising the vacuum pump 21, or may be wholly or partially embedded in or attached to the casing of the vacuum pump 21. The electronic processor 30, the display means 40, 41, the audio output means 50, 51, and the electronic input means 60, 61, 65, are provided with electrical energy required for their operation by a power supply 26. Preferably, the power supply 26 is the same power supply unit that powers the medical device 20, so that a separate power supply 26 dedicated solely to the electronic processor 30 is not necessary. In such cases, the power supply 26 may typically be a battery (not illustrated) or an external source of power, such as electricity supplied by a standard 120 volt, 60 Hz AC outlet (not illustrated). Additional electronic circuitry and components (such as transformers or converters) may be required to step-up or step-down the electrical current supplied by the power supply 26 for use by the electronic processor 30 and the components of the appliance 10 that it controls. Where a separate, dedicated power supply 26 is necessary, the power supply 26 may be comprised of one or more of almost any compact, portable source of electrical energy known in the relevant art or developed in the relevant art in the future, such as a battery. In other embodiments of the invention, the power supply 26 may also be comprised of one or more devices that are used to collect solar or other electromagnetic energy and convert such energy to a form appropriate for powering the electronic processor 30 and the components of the appliance 10 that it controls. For example, the power supply 26 may be comprised of one or more photoelectric cells fabricated from a silicon compound. The type of power supply 26 to be used in any particular embodiment of the appliance 10 is dependent upon the anticipated use of the appliance 10 and the individual preference of the user of the appliance 10. Preferably, the power supply 26 is a re-chargeable lithium-ion battery that is rechargeable by connecting it to a standard 120 volt, 60 Hz AC outlet. The power supply 26 is electronically connected to the electronic processor 30 by one or more circuit elements 29 (illustrated schematically in FIG. 2, but not illustrated in FIG. 1), as described in more detail below. Some embodiments of the appliance 10 may also include power reduction means (not illustrated) to decrease the consumption of electrical power by the components of the appliance 10 other than the medical device 20. An example of such means is described in U.S. Pat. No. 5,931,764 to Viztec, Inc., which is incorporated herein by reference. Other embodiments may also include means to recharge the power supply 26, such as the use of direct electrical contacts, RF signals, inductive, solar-galvanostatic, potentiostatic, and other charging means currently known in the relevant art or developed in the relevant art in the future. To accomplish such charging, the power supply 26 or the electronic processor 30 may include a regulator control circuit that accepts current and voltage from an external power source for storage in the power supply 26. An example of such means is described in U.S. Pat. No. 5,931,764 to Viztec, Inc., which is incorporated herein by reference.

In the embodiment of the invention illustrated in FIG. 1 and FIG. 2, the appliance 10 further comprises electronic control means 80, which enable the user of the appliance 10 to control or provide other input regarding the various functions performed by the electronic processor 30. For example, in the embodiment of the invention illustrated in FIG. 1 and FIG. 2, the appliance 10 generally has an on/off switch 27, which is comprised of a standard toggle-type of electrical switch, and is used to turn the electronic processor 30 on and off. In addition, the appliance includes a knob 28, which may be used to select various portions of the video content and audio content available for display on the display means 40, 41 and broadcast over the audio output means 50, 51. Other embodiments of the invention may also comprise other electronic control means 80, which may include any suitable means that are currently known in the relevant art or that may be developed in the relevant art in the future to provide data or control input in electronic form. Examples of such means include rheostats, potentiometers, switches, relays, touch screen LCD's, and other input means, and combinations of the foregoing. Another example is a voice activated electronic control means 80. For example, where the audio output means 50, 51 is comprised of a piezoelectric device 51 that may act as both a speaker and a microphone, the piezoelectric device 51 may be used to receive voice commands from the user of the appliance 10 and convert those commands to digital signals that are electronically transferred to the electronic processor 30. The electronic processor 30 may then convert the digital signals to electronic commands that govern the operation of the electronic processor 30, allowing for hands-free operation of the informational aspect of the appliance 10. The electronic control means 80 are electronically connected to the electronic processor by one or more circuit elements, as described in more detail below. For example, in the embodiment of the invention illustrated in FIG. 1 and FIG. 2, the switch 27 and the knob 28 are connected to the electronic processor 30 by insulated copper wires 81 (illustrated schematically in FIG. 2, but not illustrated in FIG. 1).

In the embodiment of the invention illustrated in FIG. 1 and FIG. 2, the appliance 10 is also comprised of electronic input means 60 (illustrated as DVD drive 61 and USB port 65 in FIG. 1, and schematically as "Input Port" in FIG. 2), and electronic storage devices (illustrated as DVD 71 and flash storage device 75 in FIG. 1, and schematically as "Storage Device" in FIG. 2). Generally, each electronic storage device 70, 71, 75 digitally stores audio content and video content comprising the training materials and corresponds to a compatible electronic input means 60, 61, 65, respectively. For example, the electronic input receptacle DVD drive 61 is used with the DVD 71 and the flash storage device 75 is used with the electronic input receptacle USB port 65. It is to be noted that the audio content and video content comprising the training materials may be stored on more than one electronic storage device 70, 71, 75. The DVD drive 61 and the USB port 65, as well as their corresponding DVD 71 and flash storage device 75, respectively, are well known in the art. In other embodiments of the invention, the electronic storage devices 70, 71, 75 and their corresponding compatible electronic input means 60, 61, 65 may be comprised of any suitable means currently known in the relevant art (such as floppy discs and compact discs) or developed in the relevant art in the future that may be used for storing electronic data in digital form. More than one type of electronic storage device 70, 71, 75 and corresponding compatible electronic input means 60, 61, 65 may be used with any particular embodiment of the appliance 10. The preferred type and number of electronic storage devices 70, 71, 75 and corresponding compatible electronic input means 60, 61, 65 to be utilized in any particular embodiment of the appliance 10 is dependent upon the size and complexity of the medical device 20, the type and quantity of audio content and video content involved, the preference of the user of the appliance 10, and other factors. Further, the electronic input means 60, 61, 65 may be placed in any suitable position on the surface of the medical device 20. The electronic input means 60, 61, 65 are electronically connected to the electronic processor 30 by one or more circuit elements, as described in more detail below. For example, in the embodiment of the invention illustrated in FIG. 1 and FIG. 2, the electronic input means 60, 61, 65 are connected to the electronic processor 30 by insulated copper wires 69 (illustrated schematically in FIG. 2, but not illustrated in FIG. 1).

In the embodiment of the invention illustrated in FIG. 1 and FIG. 2, the appliance 10 is comprised of display means 40, 41, which receive data and information (as video content) from the electronic processor 30 and optically display such data and information in a format that may be observed from above the surface of the appliance 10. In other embodiments of the invention, the appliance 10 may have two or more electronic displays 41 comprising the display means 40. The number of electronic displays 41 is generally dependent upon the physical shape and configuration of the appliance 10, the position of the user of the appliance 10 while the appliance 10 is in use, the preferences of the user of the appliance 10, and other factors. Preferably, a single electronic display 41 displays all data and information comprising the video content supplied by the electronic processor 30. The electronic display 41 is electronically connected to the electronic processor 30 by one or more circuit elements 42 (illustrated schematically in FIG. 2, but not illustrated in FIG. 1), as described in more detail below.

In the embodiments of the invention illustrated in FIG. 1 and FIG. 2, the display means 40, 41 are comprised of an LCD display. In other embodiments of the invention, the display means 40, 41 may be comprised of any suitable type of miniature, portable display device currently known in the relevant art or developed in the relevant art in the future that is capable of receiving data and information from the one or more electronic processors and displaying such data and information in a format that may be optically observed. For example, the display means 40, 41 may be comprised of LED, plasma, electronic papers (e.g., GYRICON, choleteric nematic phase transition, and IRIDIGM), and similar types of displays. The type of display means 40, 41 is dependent upon the preferences of the user of the appliance 10, the functions to be performed by the appliance 10, the video content to be displayed by the display means 40, 41, the expected use of the appliance 10, and other factors. It is to be noted that more than one type of display means 40, 41 may be used in the various embodiments of the invention. It is also to be noted that the display means 40, 41 may be of almost any shape currently known in the relevant art or developed in the relevant art in the future. For example, the electronic display 41 of the appliance 10 illustrated in FIG.

1 is generally rectangular in shape. In addition, in various embodiments of the invention, the display means 40, 41 may display data and information in any format desired by the user of the appliance 10. For example, the electronic display 41 in the embodiment illustrated in FIG. 1 may display a video of a person explaining a particular feature of the medical device 20 on the top portion thereof, while data and information related to operation of the medical device 20 (such as a chart of negative pressure level variance over time) is displayed on the bottom portion thereof.

Preferably, as illustrated in FIG. 1, the display means 40, 41 of the appliance 10 has one electronic display 41 that is comprised of an LCD electronic display 41. Referring to the embodiment of the invention illustrated in FIG. 1 and FIG. 2 as an example, the LCD electronic display 41 may be constructed of rigid, semi-rigid, or flexible materials, such as glass and suitable transparent polymers (e.g., polyvinyl chloride or polycarbonate). The type of material used to construct the LCD electronic display 41 is dependent upon the anticipated use of the appliance 10, the desired flexibility of the appliance 10, the desired aesthetic appearance of the appliance 10 in accordance with the individual taste of the user of the appliance 10, and other factors. In different embodiments of the invention, the LCD electronic display 41 may provide information in full-motion video, in static display, in black and white, and in one or more colors and combinations of colors and different shades of the same color. In addition, the LCD electronic display 41 may be constructed of bi-stable or multi-stable display material, such as a ferroelectric LCD based upon smectic liquid crystals typically of the C phase that exhibit chiral behavior, that will maintain an image when power has been removed. In addition, the LCD electronic display 41 may be constructed in a manner so that it provides stereoscopic effects, such as images that appear three-dimensional and images that alter their appearance based upon a viewing angle. This type of display is described in U.S. Pat. No. 5,931,764 to Viztec, which is incorporated herein by reference. Further, the LCD electronic display 41 may incorporate a "touch screen" feature (as all or a portion of the electronic control means 80), so that data may be input into the electronic processor 30 by touching a portion of the surface of the LCD electronic display 41. Resistive, projected, surface capacitive, IR, surface wave, and other similar types of LCD displays currently known in the relevant art or developed in the relevant art in the future may be used for this purpose. More preferably, the LCD electronic display 41 is an LCD utilizing continuous grain silicon technology.

In the embodiment of the invention illustrated in FIG. 1 and FIG. 2, the appliance 10 further comprises audio output means 50, 51. The audio content of the training materials is transferred from the electronic processor 30 to the audio output means 50, 51 so that it may be audibly broadcast to the user of the appliance 10. In the illustrated embodiment, the audio output means 50, 51 is comprised of thin-film flexible piezoelectric speaker 51 that offers multiple-octave sound. A suitable piezoelectric speaker/microphone made of polymer films is described in U.S. Pat. No. 5,115,472, which is incorporated herein by reference. In other embodiments, the audio output means 50, 51 may be comprised of any suitable speaker-type device (such as standard magnet-based speakers or headphones) or combinations of such devices currently known in the relevant art or that may be developed in the relevant art in the future. The audio output means 50, 51 is electronically connected to the electronic processor 30 by one or more circuit elements 52 (illustrated schematically in FIG. 2, but not illustrated in FIG. 1), as described in more detail below.

The electronic processor 30 is electronically connected to the display means 40, 41, the audio output means 50, 51, and the electronic input means 60, 61, 65 by one or more circuit elements 29, 42, 52, 69, 81. For example, in the embodiment of the invention illustrated in FIG. 1 and FIG. 2, circuit elements 29, 42, 52, 69, 81 are generally comprised of electrically conductive wires or ribbons. In other embodiments of the invention, the one or more circuit elements 29, 42, 52, 69, 81 may be any suitable electrically conductive connectors currently known in the relevant art or that may be developed in the relevant are in the future, such as electrically conductive ribbons, strips, inks and similar connectors and combinations thereof. For example, the electronic processor 30 may be connected to the electronic display 41 by circuit elements 42 comprised of direct electrical contact between the leads on the circuits comprising the electronic processor 30 and the leads on the electronic display 41 in cases where the electronic processor 30 and the electronic display 41 are integrated as a single unit. The preferred circuit elements 29, 42, 52, 69, 81 are dependent upon the nature of the device to be connected to the electronic processor 30, the design, relative position, and configuration of such devices and the circuit elements 29, 42, 52, 69, 81, and other factors. The preferred circuit elements 29, 42, 52, 69, 81 are a direct electrical contact between the electronic processor 30 and the devices to which it is connected using the circuit elements 29, 42, 52, 69, 81, respectively.

The present invention also includes a method of instructing a user of the appliance 10 how to use and operate the appliance 10 (and the medical device 20, in particular) for purposes of providing medical treatment to a person. Generally, the method comprising the following actions. First, the user of the appliance 10 gains physical access to the appliance 10. Second, the user activates the electronic processor 30 by means of the electronic control means 80, 27, 28, so that the video content is displayed on the electronic display 40, 41. Third, the user of the appliance 10 visually observes the video content displayed on the electronic display 40, 41 to gain knowledge regarding use and operation of the medical device 20 for purposes of using the medical device 20 to provide medical treatment to the person. In some embodiments, the medical device 20 used in the method further comprises a vacuum pump 21 used to provide suction for purposes of the medical treatment, and the medical treatment comprises negative pressure wound therapy. In other embodiments, the method further comprises the action of the user using the medical device 20 to provide medical treatment to the person.

Another method of instructing a user of the appliance 10 how to use and operate the appliance 10 for purposes of providing medical treatment to a person generally comprises the following actions. First, the user of the appliance 10 gains physical access to the appliance 10. Second, the user operably connects the electronic storage device 70, 71, 75 to the corresponding electronic input means 60, 61,65, respectively. Third, the user activates the electronic processor 30 by means of the electronic control means 80, 27, 28, so that the video content is displayed on the electronic display 40, 41. Fourth, the user of the appliance 10 visually observes the video content displayed on the electronic display 40, 41 to gain knowledge regarding use and operation of the medical device 20 for purposes of using the medical device 20 to provide medical treatment to the person. In some embodiments, the medical device 20 used in the method further comprises a vacuum pump 21 used to provide suction for purposes of the medical treatment, and the medical treatment comprises negative pressure wound therapy. In other embodiments, the method further comprises the action of the user using the medical device 20 to provide medical treatment to the person.

What is claimed is:

1. A negative pressure wound therapy apparatus comprising:
   a negative pressure source configured to supply negative pressure to a dressing covering a wound;
   a storage device configured to store video content comprising user instructions for using and operating the apparatus;
   an electronic controller in communication with the storage device; and
   a display in communication with the electronic controller, the display configured to output the video content stored in the storage device,
   wherein:
      the electronic controller is configured to (i) receive an input from a user and (ii) cause the display to output the video content comprising the user instructions for using and operating the apparatus; and
      the video content is indexed so that different portions of the user instructions for using and operating the apparatus are configured to be selected by a user using the apparatus.

2. The apparatus of claim 1, wherein the electronic controller is further configured to cause the display to output the user instructions for using and operating the apparatus in response to the input from the user.

3. The apparatus of claim 1, wherein the display comprises a touch screen display, and wherein the touch screen display comprises a user interface configured to permit the user to provide the input.

4. The apparatus of claim 1, wherein the display comprises a color display.

5. The apparatus of claim 1, wherein the apparatus further comprises an audio output device in communication with the electronic controller, and the electronic controller is further configured to cause at least one of the audio output device or the display to output at least one alarm notification associated with the supply of negative pressure.

6. The apparatus of claim 1, wherein the user instructions for operating the apparatus further comprise audio content.

7. The apparatus of claim 1, wherein the apparatus further comprises an audio output device configured to output at least a portion of audio associated with the video content.

8. The apparatus of claim 1, further comprising a power supply configured to provide electrical power to the apparatus.

9. The apparatus of claim 1, further comprising a port configured to receive an external storage device.

10. The apparatus of claim 9, wherein the port is at least one of a Universal Serial Bus (USB) port or a flash storage device port.

11. The apparatus of claim 1, wherein the user instructions for using and operating the apparatus further comprise instructions for resolving an alarm notification associated with the supply of negative pressure.

12. A method of operating a negative pressure wound therapy apparatus comprising a negative pressure source, an electronic processor, a storage device, user instructions on the storage device comprising full-motion video for using and operating the apparatus, and an output interface, the method comprising:
   by the electronic processor, selecting a desired portion of the user instructions comprising full-motion video for using and operating the apparatus on the storage device to be output on the output interface;
   outputting on the output interface the desired portion of the user instructions comprising full-motion video for using and operating the apparatus to permit a user to gain knowledge regarding use and opera apparatus to provide medical treatment; and
   by the electronic processor, activating the negative pressure wound therapy apparatus to provide suction to a wound dressing covering a wound;
   wherein outputting on the output interface the desired portion of the user instructions comprising full-motion video for using and operating the apparatus is completed before activating the negative pressure wound therapy apparatus to provide suction to the wound dressing.

13. The method of claim 12, further comprising, by the electronic processor, receiving input from the user, the input comprising the desired portion of the user instructions for using and operating the apparatus, and outputting the user instructions for using and operating the apparatus in response to the input.

14. The method of claim 12, wherein the user instructions for using and operating the apparatus further comprise audio and/or visual content.

15. The method of claim 14, wherein the audio and/or visual content comprises one or more of full-motion video, graphics, drawings, slides, charts, plans, or specifications.

16. The method of claim 14, wherein the output interface comprises an audio output device and the method further comprises outputting at least a portion of the audio and/or visual content to the audio output device.

17. The method of claim 12, comprising outputting on the output interface at least one alarm notification associated with supplying negative pressure.

18. The method of claim 12, wherein the user instructions for using and operating the apparatus comprise instructions for resolving an alarm notification associated with supplying negative pressure.

19. A negative pressure wound therapy system comprising:
   a vacuum suction device;
   a storage device configured to store media comprising user instructions including training materials for the use and operation of the negative pressure wound therapy system, wherein the training materials comprise one or more troubleshooting guides;
   a display configured to present the media to a user; and
   an electronic processor integrated with the vacuum suction device, the electronic processor configured to output the media to the display and receive a selection from the user to view a desired user instruction comprising one or more troubleshooting guides from the training materials.

20. The system of claim 19, further comprising a graphical user interface, wherein the system is configured to execute software.

21. The system of claim 20, wherein the graphical user interface comprises a display.

22. The system of claim 19, wherein the media stores information that enables provision of wound therapy.

23. The system of claim 19, wherein the system is configured to output audio.

24. The system of claim 19, wherein the system is configured to output audio from an external device.

25. The apparatus of claim 1, wherein the user instructions are configured to provide bi-directional communication with the user, thereby permitting the user to engage in an interactive dialogue with the apparatus.

26. The apparatus of claim 1, wherein the electronic controller is further configured to cause the display to output a portion of the video content in response to the input from the user, the input associated with a user selection of the portion of the video content.

27. The system of claim 12, the full-motion videos are indexed to permit the user to select the desired video.

28. The system of claim 19, wherein the troubleshooting guides comprise full motion videos.

\* \* \* \* \*

UNITED STATES PATENT AND TRADEMARK OFFICE
CERTIFICATE OF CORRECTION

PATENT NO. : 10,675,389 B2
APPLICATION NO. : 15/693267
DATED : June 9, 2020
INVENTOR(S) : Weston et al.

Page 1 of 1

It is certified that error appears in the above-identified patent and that said Letters Patent is hereby corrected as shown below:

In the Claims

In Column 14, Line 8, Claim 12, delete "opera" and insert --operation of the--.

Signed and Sealed this
Thirteenth Day of October, 2020

Andrei Iancu
*Director of the United States Patent and Trademark Office*